(12) United States Patent
You et al.

(10) Patent No.: US 11,497,659 B2
(45) Date of Patent: Nov. 15, 2022

(54) ABSORBENT ARTICLE HAVING ELASTOMERIC PANELS

(71) Applicant: Kimberly-Clark Worldwide, Inc., Neenah, WI (US)

(72) Inventors: KueYoung You, Seongnam-si (KR); MinJae Lee, Yongin-si (KR); JiYoung Haley Jung, SeongNam-si (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 445 days.

(21) Appl. No.: 16/612,077

(22) PCT Filed: Mar. 21, 2018

(86) PCT No.: PCT/US2018/023574
§ 371 (c)(1),
(2) Date: Nov. 8, 2019

(87) PCT Pub. No.: WO2018/226289
PCT Pub. Date: Dec. 13, 2018

(65) Prior Publication Data
US 2020/0138641 A1     May 7, 2020

Related U.S. Application Data

(60) Provisional application No. 62/517,720, filed on Jun. 9, 2017.

(51) Int. Cl.
*A61F 13/49*     (2006.01)
*A61F 13/496*    (2006.01)

(52) U.S. Cl.
CPC .... *A61F 13/49012* (2013.01); *A61F 13/4902* (2013.01); *A61F 13/496* (2013.01)

(58) Field of Classification Search
CPC .......... A61F 13/49012; A61F 13/49011; A61F 13/4902; A61F 13/49
See application file for complete search history.

(56) References Cited

U.S. PATENT DOCUMENTS

| | | |
|---|---|---|
| 6,083,212 A | 7/2000 | Kumasaka |
| 6,991,623 B2 | 1/2006 | Tanaka et al. |
| 7,000,260 B2 | 2/2006 | Rajala et al. |

(Continued)

FOREIGN PATENT DOCUMENTS

| | | |
|---|---|---|
| CN | 103391762 A | 11/2013 |
| EP | 1257240 B1 | 1/2007 |

(Continued)

*Primary Examiner* — Nicholas J. Weiss
*Assistant Examiner* — Roy Kim
(74) *Attorney, Agent, or Firm* — Kimberly-Clark Worldwide, Inc.

(57) ABSTRACT

A garment-like absorbent article can have a front region, a back region, and a central region extending between and connecting the front region and the back region. The front region and the back region of the absorbent article can be formed from a combination of elastic materials. The combination of the elastic materials can be asymmetrically configured about the absorbent article to provide an improved fit of the absorbent article to the body of the wearer as well as to provide the wearer with an absorbent article that resembles traditional woven underwear.

12 Claims, 6 Drawing Sheets

(56) References Cited

U.S. PATENT DOCUMENTS

| | | |
|---|---|---|
| 7,217,261 B2 | 5/2007 | Otsubo et al. |
| 7,749,211 B2 | 7/2010 | Van Gompel et al. |
| 7,803,244 B2 | 9/2010 | Siqueira et al. |
| 8,147,476 B2 | 4/2012 | Veith et al. |
| 8,277,430 B2 | 10/2012 | Tabor et al. |
| 8,753,466 B2 | 6/2014 | Thorson |
| 8,915,900 B2 | 12/2014 | Shimada et al. |
| 9,433,539 B2 | 9/2016 | Veith et al. |
| 2002/0147438 A1 | 10/2002 | Tanaka et al. |
| 2004/0127880 A1 | 7/2004 | Weber |
| 2005/0055001 A1 | 3/2005 | Cazzato et al. |
| 2005/0148974 A1 | 7/2005 | Datta et al. |
| 2007/0032766 A1 | 2/2007 | Liu et al. |
| 2010/0312214 A1 | 12/2010 | Shimada et al. |
| 2011/0098668 A1* | 4/2011 | Thorson ............ A61F 13/49058 604/385.24 |
| 2014/0330236 A1* | 11/2014 | Schonbeck ............. A61L 15/24 604/385.16 |
| 2016/0058628 A1* | 3/2016 | Morimoto ......... A61F 13/49012 604/372 |
| 2016/0184145 A1* | 6/2016 | Morimoto ............. A61F 13/496 604/385.29 |

FOREIGN PATENT DOCUMENTS

| | | |
|---|---|---|
| EP | 2215999 B1 | 12/2013 |
| EP | 2221031 B1 | 7/2017 |
| WO | 04021945 A1 | 3/2004 |
| WO | 07008127 A1 | 1/2007 |
| WO | 07069225 A2 | 6/2007 |
| WO | 08143951 A1 | 11/2008 |
| WO | 16108898 A1 | 7/2016 |

\* cited by examiner

ABSORBENT ARTICLE HAVING ELASTOMERIC PANELS

BACKGROUND OF THE DISCLOSURE

Child care, feminine care, and adult hygiene-related absorbent personal care articles are often used to protect a wearer's outer garments from soiling, and to collect and retain body exudates such as menses, blood, feces, and urine. Such articles are often presented in disposable garment-like product formats (as opposed to inserts, pads, or liners) and are worn as undergarments in the place of traditional underwear. They are most commonly placed on a wearer by being pulled up about a wearer's legs towards the wearer's lower abdomen and placed adjacent a wearer's crotch region during use.

Today, many wearers of absorbent garment-like articles include adults who experience various forms of incontinence. Primary desired attributes of such garments include the garment retaining body exudate, minimal or no leakage of body exudate, close-to-body fit of the garment, and that it resembles traditional woven underwear. Consumers are interested in such attributes as there is a desire to enhance the overall personal experience of using such products while reducing incontinence-related stigmas. Consumers want a garment that will meet their needs without signaling to others that they are wearing such absorbent garment-like articles. Absorbent article stigmas are aggravated by product designs which can feel bulky when in use, are ill-fitting and uncomfortable for the wearer to wear, do not fit close to the body and, therefore, may gap away from the wearer's body producing an outline that can be seen through a wearer's clothing, may be manufactured from materials that can create relatively high levels of noise during use due to the specific product construction materials, and by an overall artificial visual appearance of such products when viewed by the wearer and also by third parties.

In order to improve the fit of garment-like articles, many garment-like articles are formed by positioning an absorbent assembly between or otherwise bonded to at least one stretchable or elastomeric outer layer of the garment-like article. The stretchable or elastomeric outer layer can extend laterally and longitudinally beyond the dimensional boundaries of the absorbent assembly such as into the waist region of the garment or into areas that would contact a wearer's hips when the garment is worn. Generally, the usage of the stretchable or elastomeric layer has been symmetrical within an absorbent garment. However, the wearers of absorbent articles have body shapes in a variety of shapes, sizes, and curvature, and are generally not symmetrical. Such a symmetrical product placed on a non-symmetrical body can result in a reduction in proper fit of the garment on the body of the wearer. An absorbent article created with symmetrical tensioning and stretch of an elastomeric material, when placed on a non-symmetrical body of a wearer, can cause the wearer to experience divergent and/or convergent tensioning of the absorbent garment on their body depending upon the curvature of the body of the wearer. For example, areas of the wearer's body with a larger circumference, such as, for example, the belly and/or buttocks regions, may experience higher tension from the absorbent article which can result in discomfort due to a tight fit. As an additional example, areas of the wearer's body with smaller circumference, such as, the lower hip and/or around the legs, may experience lower tension from the absorbent article and may fit loosely on these regions of the wearer's body resulting in leakage of body exudate. Such an ill-fitting product can increase the incidents of exudate leakage. As an additional example, some portions of the absorbent article may buckle due to an ill fit between the absorbent article and the body of the wearer.

There is need for an absorbent article having an improved fit about the lower torso of the wearer. There is a need for an absorbent article having asymmetrical placement of elastomeric material to provide for targeted placement of the elastomeric material having different elastomeric functionality. Such is desirable so as to provide a more conformable fit across different areas of a wearer's anatomy. There is a need to provide an absorbent article having an improved fit as well as the appearance of traditional woven underwear.

SUMMARY OF THE DISCLOSURE

In various embodiments, an absorbent article can have a front region comprising a front panel comprising a front panel upper edge, a front panel lower edge, a first front side edge, and a second front side edge; a first longitudinal length between the front panel upper edge and the front panel lower edge; a first elastomeric panel comprising a first material selected from an elastomeric film, an elastomeric nonwoven web or a laminate of at least one elastomeric polymeric film layer and at least one nonwoven web layer; a first laminate comprising elastomeric strands and a nonwoven layer and defining a front waist portion having a front waist portion longitudinal length and a front central chassis portion having a front central chassis portion longitudinal length; a back region comprising a back panel comprising a back panel upper edge, a back panel lower edge, a first back side edge, and a second back side edge; a second longitudinal length between the back panel upper edge and the back panel lower edge; a second elastomeric panel comprising a second material selected from an elastomeric film, an elastomeric nonwoven web or a laminate of at least one elastomeric polymeric film layer and at least one nonwoven web layer; a second laminate comprising elastomeric strands and a nonwoven layer and defining a back waist portion having a back waist portion longitudinal length and a back central chassis portion having a back central chassis portion longitudinal length, wherein the back central chassis portion longitudinal length is greater than the front central chassis portion longitudinal length; and a central region extending between and comprising an absorbent assembly.

In various embodiments, the front waist portion longitudinal length is the same as the back waist portion longitudinal length. In various embodiments, the first elastomeric panel has a longitudinal length that is greater than a longitudinal length of the second elastomeric panel. In various embodiments, the longitudinal length of the first elastomeric panel is from about 60% to about 66% of the first longitudinal length of the front panel. In various embodiments, the longitudinal length of the second elastomeric panel is from about 53% to about 59% of the second longitudinal length of the back panel. In various embodiments, the front central chassis portion longitudinal length is from about 15% to about 25% of the first longitudinal length of the front panel. In various embodiments, the back central chassis portion longitudinal length is from about 26% to about 36% of the second longitudinal length of the back panel.

In various embodiments, the front waist portion comprises multiple elastomeric strands which are parallel to each other and uniformly spaced from each other. In various embodiments, the spacing between each of the elastomeric strands of the front waist portion is less than 5 mm. In various embodiments, the front central chassis portion comprises multiple elastomeric strands which are parallel to teach other and uniformly spaced from each other. In various embodiments, the spacing between each of the elastomeric strands of the front central chassis portion is at least 5 mm.

In various embodiments, the front waist portion and the back waist portion combine to form a waist region and wherein the front elastomeric panel and the back elastomeric panel combine to form an elastomeric panel region and a load at 50% strain of the waist region is greater than or equal to a load at 50% strain of the elastomeric panel region. In various embodiments, the front chassis portion and the back chassis portion combine to form a chassis region and a load at 50% strain of the chassis region is less than the load at 50% strain of the waist region and the elastomeric panel region.

Repeat use of reference characters in the present specification and drawings is intended to represent the same or analogous features or elements of the disclosure.

DETAILED DESCRIPTION OF THE DISCLOSURE

The present disclosure is directed towards an absorbent article such as a garment-like absorbent article. The absorbent article has a front region, a back region, and a central region extending between and connecting the front region and the back region. The front region and the back region of the absorbent article can be formed from a combination of elastomeric materials. The combination of the elastomeric materials can be asymmetrically configured about the absorbent article to provide an improved fit of the absorbent article to the body of the wearer as well as to provide the wearer with an absorbent article that resembles traditional woven underwear.

Definitions

As used herein, the term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, enuresis garments, menstrual pants, and adult incontinence garments, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Absorbent Article:

The present disclosure is directed towards an absorbent article such as a garment-like absorbent article. The absorbent article has a front region, a back region, and a central region extending between and connecting the front region and the back region. The front region and the back region of the absorbent article can be formed from a combination of elastomeric materials. The combination of the elastomeric materials can be asymmetrically configured about the absorbent article to provide an improved fit of the absorbent article to the body of the wearer as well as to provide the wearer with an absorbent article that resembles traditional woven underwear.

Figure 1:
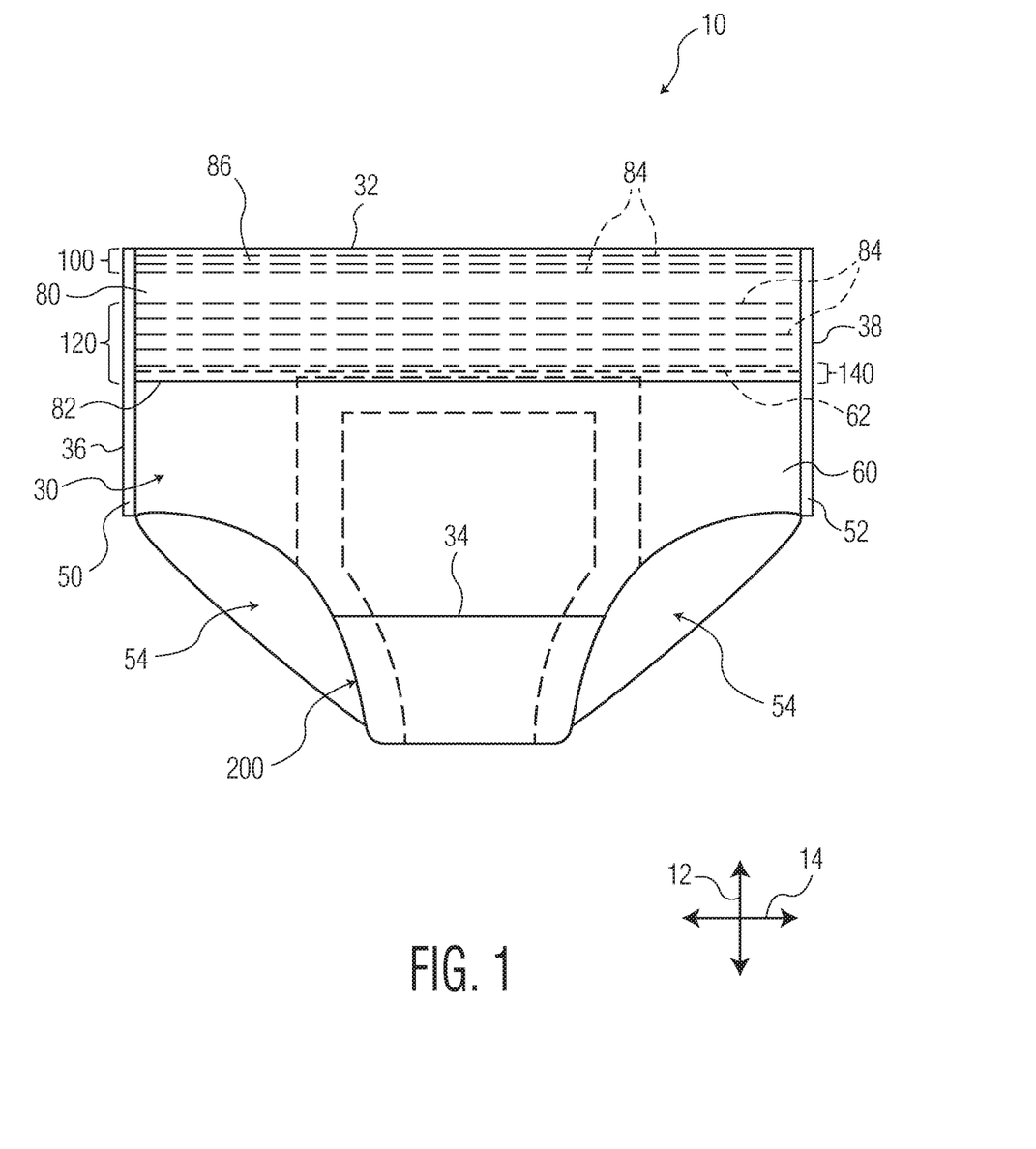
FIG. 1 provides a front view of an embodiment of an absorbent article.
Figure 2:
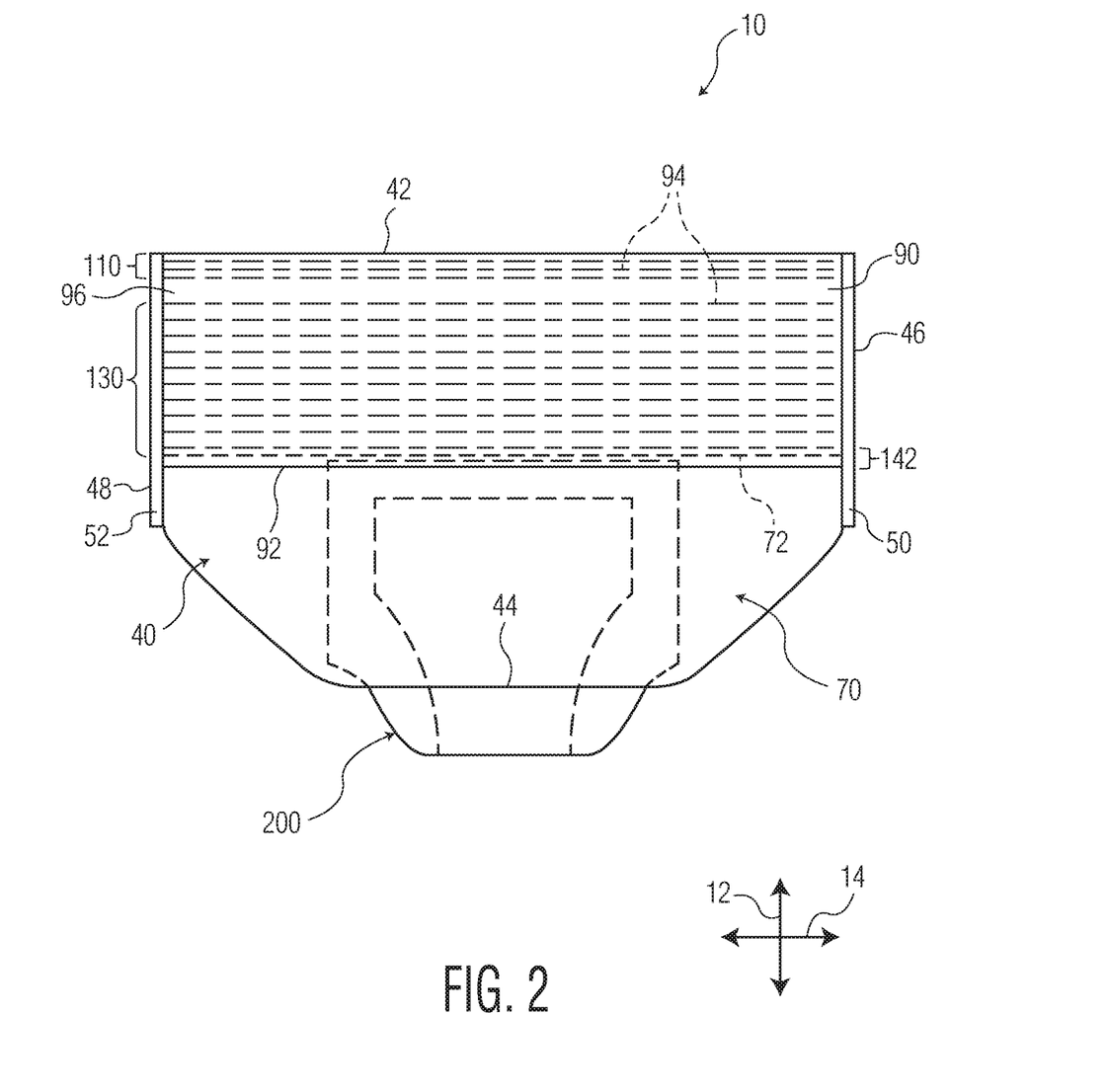
FIG. 2 provides a back view of the absorbent article of FIG. 1.
Figure 3:
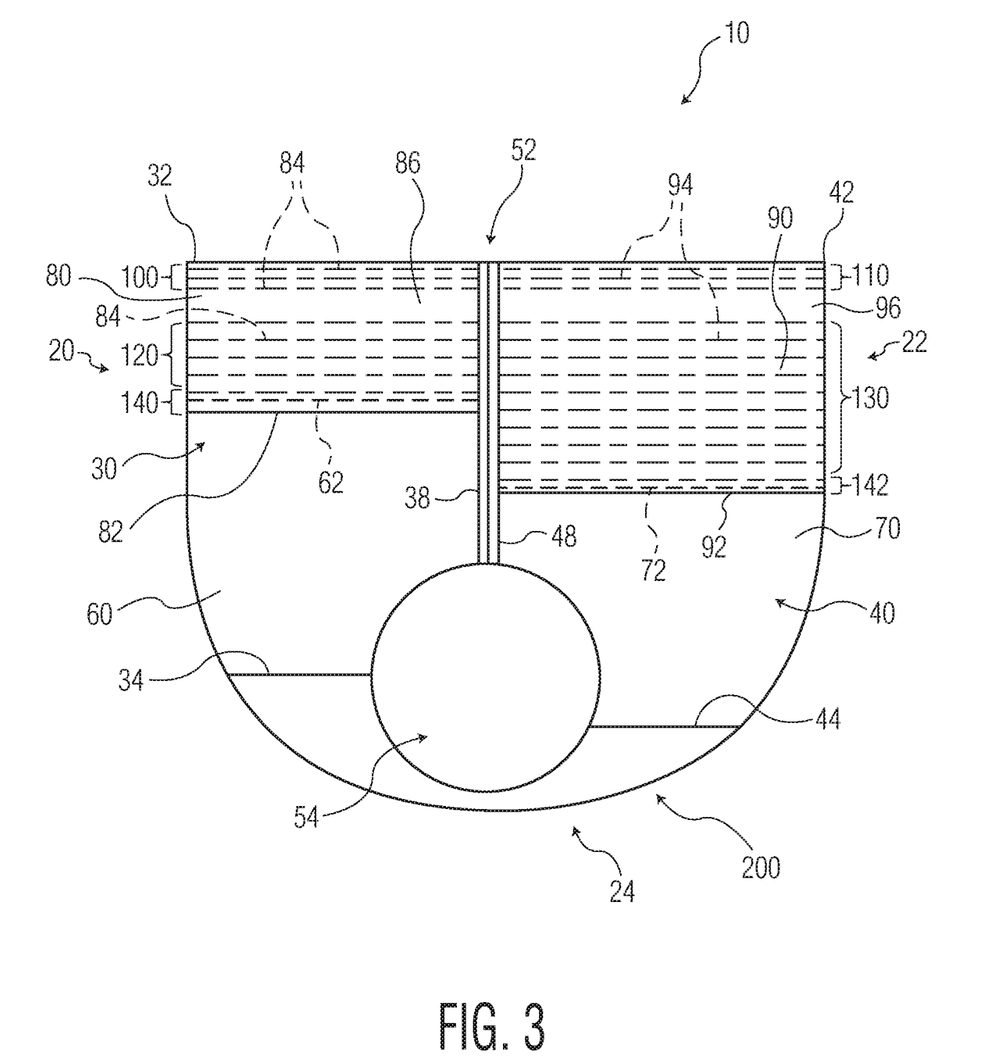
FIG. 3 provides a side view of the absorbent article of FIG. 1.
Figure 4:
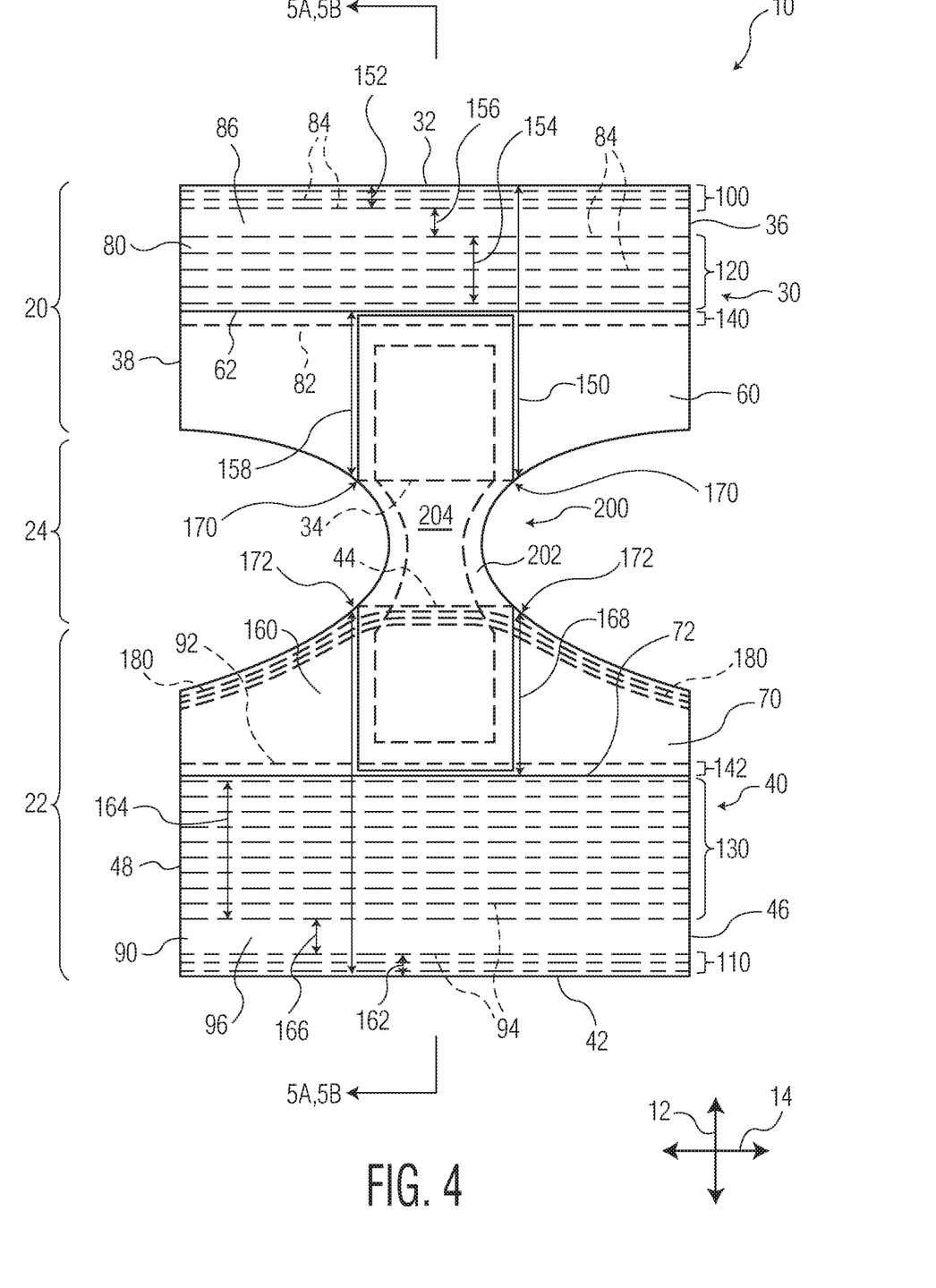
FIG. 4 provides a longitudinally and transversely stretched and laid-flat configuration of the absorbent article of FIG. 1 prior to the joining of the front and back regions.
Figure 5A:
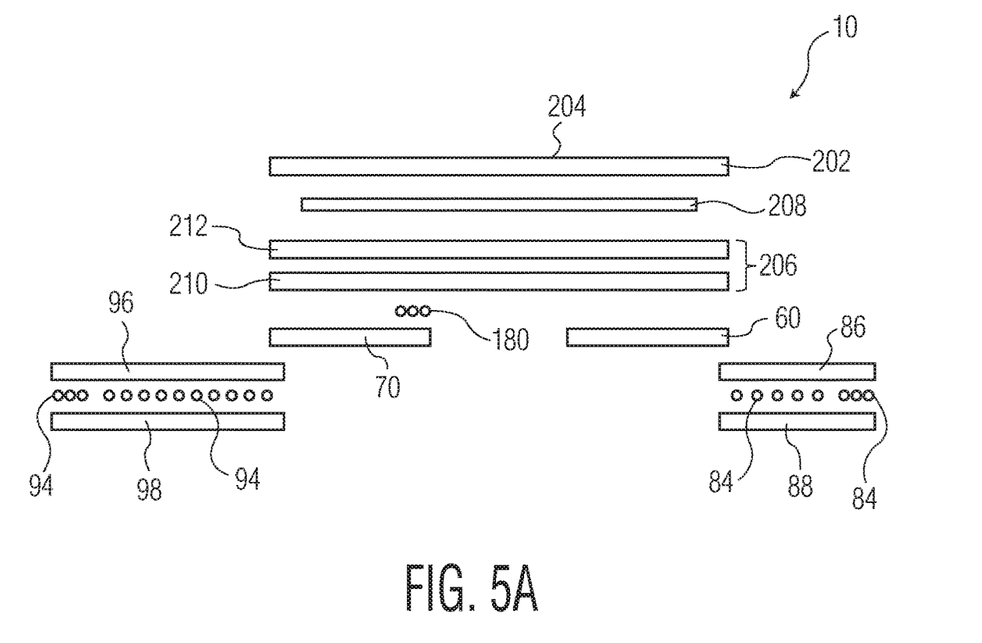
FIG. 5A and FIG. 5B provide embodiments of cross-sectional views of the absorbent article of FIG. 4 taken along lines 5A-5A and 5B-5B, respectively.
Figure 5B:
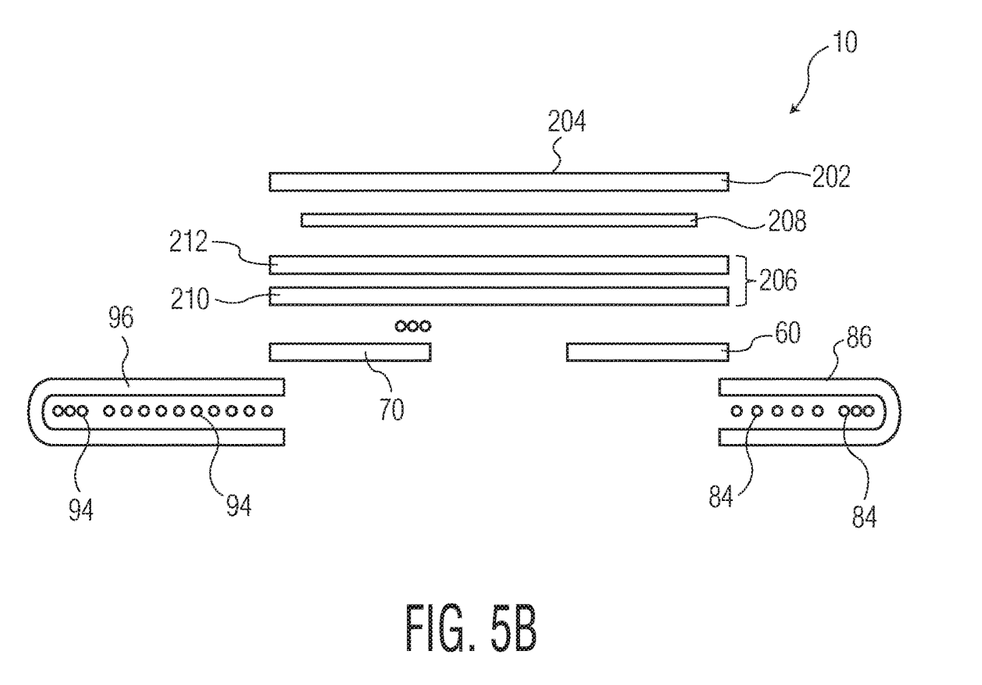

Referring to FIGS. 1-5B, an illustration of an exemplary embodiment of an absorbent article 10 is illustrated. FIG. 1 provides a front view of the absorbent article 10 in a pull-on, garment-like configuration, FIG. 2 provides a back view of the absorbent article 10 of FIG. 1, FIG. 3 provides a side view of the absorbent article 10 of FIG. 1, FIG. 4 provides an illustration of the absorbent article 10 of FIG. 1 in a longitudinally and transversely stretched and laid-flat configuration prior to the joining of the front and back regions, 20 and 22, and FIGS. 5A and 5B provide alternative cross-sectional views of the absorbent article 10 of FIG. 4. Although for illustrative purposes certain features of the present disclosure can be described and illustrated with respect to an adult incontinence garment, the various aspects and embodiments of the present disclosure are also suitable for use with diapers, youth pants, swim pants, training pants, enuresis garments, menstrual pants, and the like.

The absorbent article 10 has a longitudinal direction 12 and a transverse direction 14. The absorbent article 10 is intended to be worn about the lower torso of a human and can have a front region 20, a back region 22, and a central region 24 extending between and connecting the front region 20 and the back region 22. The front region 20 and the back region 22 are those regions of the absorbent article 10 that are fitted circumferentially around at least the waist region of the wearer of the absorbent article 10 including, for example, the wearer's lower back, buttock, hips, and abdomen. The central region 24 of the absorbent article 10 is that region of the absorbent article 10 that will be positioned between the wearer's legs when the absorbent article 10 is fitted onto the wearer.

The front region 20 is defined by a front panel 30 which has a front upper edge 32, a front lower edge 34 longitudinally opposed to the front upper edge 32, a first front side edge 36, and a second front side edge 38 transversely opposed to the first front side edge 36. The back region 22 is defined by a back panel 40 which has a back upper edge 42, a back lower edge 44 longitudinally opposed to the back upper edge 42, a first back side edge 46, and a second back side edge 48 transversely opposed to the first back side edge 46. To place the absorbent article 10 into a suitable configuration for wearing about the lower torso of the wearer, the first front side edge 36 can be bonded to the first back side edge 46 to form a first side seam 50 and the second front side edge 38 can be bonded to the second back side edge 48 to form a second side seam 52. Forming the side seams, 50 and 52, can create a wearable absorbent article 10 having a waist opening and a pair of leg openings 54.

The front panel 30 can be constructed, at least in part, of an elastomeric panel 60. The elastomeric panel 60 present within the front panel 30 can be bordered by the front lower edge 34, a portion of the first front side edge 36, a portion of the second front side edge 38, and a panel upper edge 62. The elastomeric panel 60 present within the front panel 30 can, therefore, extend the transverse width of the front panel 30 between the first front side edge 36 and the second front side edge 38 and can include the front lower edge 34. The back panel 40 can be constructed, at least in part, of an elastomeric panel 70. The elastomeric panel 70 present within the back panel 40 can be bordered by the back lower edge 44, a portion of the first back side edge 46, a portion of the second back side edge 48, and a panel upper edge 72. The elastomeric panel 70 present within the back panel 40 can, therefore, extend the transverse width of the back panel 40 between the first back side edge 46 and the second back side edge 48 and can include the back lower edge 44.

The elastomeric panels, 60 and 70, can be elastic such that the elastomeric panels, 60 and/or 70, upon application of a stretching force, is stretchable in the transverse direction, and which upon release of the stretching force, contracts/returns at least a portion of its stretched length, desirably to its original dimension. In various embodiments, the elastomeric panel can have a laminate of at least one elastomeric polymeric film layer and at least one nonwoven web layer. In various embodiments, the elastomeric panel can have a laminate of at least one elastomeric polymeric film layer which can be sandwiched between at least two nonwoven web layers. In various embodiments, a material that can be suitable for use as the elastomeric panel 60 of the front panel 30 and/or the elastomeric panel 70 of the back panel 40 is a stretch-bonded laminate (SBL) in which an elastic core or middle layer is elongated before two opposing outer nonwoven web layers are bonded thereto. Another suitable material for the elastomeric panels 60 and/or 70 is a necked bonded laminate (NBL). The NBL material is a three layer laminate but the elastic core or middle layer is not prestretched prior to being attached to the two outer nonwoven web layers. Instead, the opposing outer nonwoven web layers are necked stretched before the elastic core or middle layer is bonded to them. Other examples of such elastomeric materials that can be used for the elastomeric panels 60 and/or 70 include a continuous filament stretch bonded laminate (CFSBL), a vertical filament laminate (VFL), a necked stretch bonded laminate (NSBL), or a necked thermal laminate (NTL). Combinations of such materials can also be used. Such materials are described in U.S. Pat. No. 4,720,415 to Vander Wielen et al., U.S. Pat. No. 5,366,793 to Fitts, et al., U.S. Pat. No. 5,385,775, to Wright, U.S. Pat. No. 6,969,441 to Welch et al., U.S. Pat. No. 6,978,486 to Zhou et al., U.S. Pat. No. 7,803,244 to Siqueira et al., and U.S. Pat. No. 5,226,992 to Morman et al., each of which are hereby incorporated by reference thereto in its entirety. The elastomeric laminates just described will typically include an elastomeric layer and at least one surface-bonded nonwoven web layer such as a meltblown, spunbond, or through-air bonded web.

In various embodiments, the elastomeric panels, 60 and/or 70, can be constructed from a monolayer or multilayer elastomeric film that is capable of being stretched in the transverse direction. In various embodiments, the elastomeric panels, 60 and/or 70, can be formed from an elastomeric nonwoven web that has multiple direction stretch capabilities or a laminate of such elastomeric film and nonwoven web materials.

The front panel 30 can be constructed, at least in part, of a laminate 80 that has multiple elastomeric strands 84 which can be sandwiched between at least one nonwoven web layer 86 wherein the nonwoven web layer 86 can be folded upon itself. In various embodiments, the laminate 80 can have multiple elastomeric strands 84 which can be sandwiched between at least two nonwoven web layers, 86 and 88. The laminate 80 present within the front panel 30 can be bordered by the front upper edge 32, a portion of the first front side edge 36, a portion of the second front side edge 38, and a laminate lower edge 82. The laminate 80 present within the front panel 30 can, therefore, extend the transverse width of the front panel 30 between the first front side edge 36 and the second front side edge 38 and can include the front upper edge 32. The back panel 40 can be constructed, at least in part, of a laminate 90 that has multiple elastomeric strands 94 which can be sandwiched between at least one nonwoven web layer 96. In various embodiments, the laminate 90 can have multiple elastomeric strands 94 which can be sandwiched between at least two nonwoven web layers, 96 and 98. The laminate 90 present within the back panel 40 can be bordered by the back upper edge 42, a portion of the first back side edge 46, a portion of the second back side edge 48, and a laminate lower edge 92. The laminate 90 present within the back panel 40 can, therefore, extend the transverse width of the back panel 40 between the first back side edge 46 and the second back side edge 48 and can include the back upper edge 42.

The elastomeric strands can be preformed from LYCRA brand fibers/yarns for example. LYCRA is a registered trademark of E.I. DuPont DeNemours Co., Wilmington, Del., U.S.A. The elastomeric strands can have a round, semi-circular, square, rectangular, oval, or other geometrical configuration. The elastomeric strands can be sandwiched between the at least one nonwoven or between at least two nonwovens with adhesive, ultrasonic bonding, heat pressure sealing, or any other means deemed suitable.

The laminates, 80 and 90, can each have a first portion, 100 and 110, respectively, which can be the waist portion of the absorbent article 10. The elastomeric strands 84 of the front waist portion 100 can be aligned parallel with each other and can be uniformly spaced apart from each other. In various embodiments, the spacing between each elastomeric strand 84 within the front waist portion 100 can be less than about 5, 4, or 3 mm. The elastomeric strands 94 of the back waist portion 110 can be aligned parallel with each other and can be uniformly spaced apart from each other. In various embodiments, the spacing between each of the elastomeric strands 94 of the back waist portion 110 can be less than about 5, 4, or 3 mm. In various embodiments, when the absorbent article 10 is in a usage configuration, the elastomeric strands 84 of the front waist portion 100 can be aligned with the elastomeric strands 94 of the back waist portion 110.

The laminates, 80 and 90, can each have a second portion, 120 and 130, respectively, which can be the central chassis portion of the front panel 30 and back panel 40, respectively. The elastomeric strands 84 of the second portion 120 of laminate 80 can be aligned parallel with each other and can be uniformly spaced apart from each other. In various embodiments, the spacing between each elastomeric strand 84 within the second portion 120 of laminate 80 can be greater than about 5, 6, 7, 8, or 9 mm. The elastomeric strands 94 of the second portion 130 of laminate 90 can be aligned parallel with each other and can be uniformly spaced apart from each other. In various embodiments, the spacing between each of the elastomeric strands 94 of the second portion 130 of laminate 90 can be greater than about 5, 6, 7, 8, or 9 mm. In various embodiments, when the absorbent article 10 is in a usage configuration, a portion of the elastomeric strands 84 of the second portion 120 of laminate 80 can be aligned with a portion of the elastomeric strands 94 of the second portion 130 of laminate 90.

As described, each of the front panel 30 and the back panel 40 can be formed from a combination of elastomeric laminates. Each of the front panel 30 and the back panel 40 can have a first portion which is elastomeric panel and a second portion which is a laminate of elastomeric strands sandwiched between at least one nonwoven web layer. To form the front panel 30, the elastomeric panel 60 can be placed into an overlapping configuration with laminate 80 and bonded to each other to form an overlap region 140. In various embodiments, the elastomeric panel 60 can overlap laminate 80 such that the elastomeric panel 60 is in contact with a garment facing surface of laminate 80, such as, for example, illustrated in FIGS. 1-5B. In various embodiments, the elastomeric panel 60 can overlap laminate 80 such that the elastomeric panel 60 can be placed in contact with a wearer facing surface of laminate 80. As laminate 80 includes upper edge 32 of the front panel 30, when laminate 80 is brought into an overlapping configuration with elastomeric panel 60, the lower edge 82 of laminate 80 and a portion of the nonwoven web layer 82 forming laminate 80 will overlap with the upper edge 62 and a portion of the elastomeric panel 60 to form the overlap region 140.

Similarly, to form the back panel 40, the elastomeric panel 70 can be placed into an overlapping configuration with laminate 90 and bonded to each other to form an overlap region 142. In various embodiments, the elastomeric panel 70 can overlap laminate 90 such that the elastomeric panel 70 is in contact with a garment facing surface of laminate 90, such as, for example, illustrated in FIGS. 1-5B. In various embodiments, the elastomeric panel 70 can overlap laminate 90 such that the elastomeric panel 70 can be in contact with a wearer facing surface of the laminate 90. As laminate 90 includes upper edge 42 of the back panel 40, when laminate 90 is brought into an overlapping configuration with elastomeric panel 70, the lower edge 92 of laminate 90 and a portion of the nonwoven web layer 92 forming laminate 90 will overlap with the upper edge 72 and a portion of the elastomeric panel 70 to form the overlap region 142. The overlap regions, 140 and 142, can have a length in the longitudinal direction 12 between the upper edges, 62 and 72, of elastomeric panels, 60 and 70, and the lower edges, 82 and 92, of laminates, 80 and 90, from about 4 or 5 mm to about 6 or 7 mm.

The assembly of the front panel 30 by bonding elastomeric panel 60 to laminate 80 can result in a front panel 30 having a longitudinal length 150 between the front upper edge 32 and the front lower edge 34. The longitudinal length 150 can be measured as the distance between the front upper edge 32 and the location 170 on the front lower edge 34 where the longitudinal direction side edges of the absorbent assembly 200 cross over the front lower edge 34. The longitudinal length 150 of the front panel 30 can be segmented into longitudinal lengths of various portions of the front panel 30—the longitudinal length 152 of the waist portion 100, the longitudinal length 154 of the central chassis portion 120, the longitudinal length 156 of the space between the waist portion 100 and the central chassis portion 120 where no elastomeric material is present, and the longitudinal length 158 of the elastomeric panel 60. The longitudinal length 158 of the elastomeric panel 60 can be measured as the distance between the elastomeric panel upper edge 62 and the location 170 on the front lower edge 34 where the longitudinal direction side edges of the absorbent assembly 200 cross over the front lower edge 34. The elastomeric panel 60 can have a longitudinal length 158 which is greater than the longitudinal length 152 of the waist portion 100. The elastomeric panel 60 can have a longitudinal length 158 which is greater than the longitudinal length 154 of the central chassis portion 120. The elastomeric panel 60 can have a longitudinal length 158 which is greater than the longitudinal length 156 of the space between the waist portion 100 and the central chassis portion 120. The longitudinal length 154 of the central chassis portion 120 is greater than the longitudinal length 152 of the waist portion 100. The longitudinal length 154 of the central chassis portion 120 is greater than the longitudinal length 156 of the space between the waist portion 100 and the central chassis portion 120.

In various embodiments, the front panel 30 can have an elastomeric panel 60 whose longitudinal length 158 can be from about 60% or 62% to about 64% or 66% of the longitudinal length 150 of the front panel 30. In various embodiments, the longitudinal length 154 of the central chassis 120 of the front panel 30 can be from about 15% or 22% to about 24% or 25% of the longitudinal length 150 of the front panel 130.

The assembly of the back panel 40 by bonding elastomeric panel 70 to laminate 90 can result in a back panel 40 having a longitudinal length 160 between the back upper edge 42 and the back lower edge 44. The longitudinal length 160 can be measured as the distance between the back upper edge 42 and the location 172 on the back lower edge 44 where the longitudinal direction side edges of the absorbent assembly 200 cross over the back lower edge 44. The longitudinal length 160 of the back panel 40 can be segmented into longitudinal lengths of various portions of the back panel 40—the longitudinal length 162 of the waist portion 110, the longitudinal length 164 of the central chassis portion 130, the longitudinal length 166 of the space between the waist portion 110 and the central chassis portion 130 where no elastomeric material is present, and the longitudinal length 168 of the elastomeric panel 70. The longitudinal length 168 of the elastomeric panel 70 can be measured as the distance between the elastomeric panel upper edge 72 and the location 172 on the back lower edge 44 where the longitudinal direction side edges of the absorbent assembly 200 cross over the back lower edge 44. The elastomeric panel 70 can have a longitudinal length 168 which is greater than the longitudinal length 162 of the waist portion 110. The elastomeric panel 70 can have a longitudinal length 168 which is greater than the longitudinal length 164 of the central chassis portion 130. The elastomeric panel 70 can have a longitudinal length 168 which is greater than the longitudinal length 166 of the space between the waist portion 110 and the central chassis portion 130. The longitudinal length 164 of the central chassis portion 130 is greater than the longitudinal length 162 of the waist portion 110. The longitudinal length 164 of the central chassis portion 130 is greater than the longitudinal length 166 of the space between the waist portion 110 and the central chassis portion 130.

In various embodiments, the back panel 40 can have a elastomeric panel 70 whose longitudinal length 168 can be from about 53% or 55% to about 57% or 59% of the longitudinal length 160 of the back panel 40. In various embodiments, the longitudinal length 164 of the central chassis portion 130 of the back panel 40 can be from about 26% or 32% to about 34% or 36% of the longitudinal length 160 of the back panel 140.

The elastomeric panel 70 of the back panel 40 can have a longitudinal length 168 which is shorter than the longitudinal length 158 of the elastomeric panel 60 of the front panel 30. The central chassis portion 130 of the back panel 40 can have a longitudinal length 164 which is greater than the longitudinal length 154 of the central chassis portion 120 of the front panel 30. The longitudinal length 152 of the waist portion 100 can be the same as the longitudinal length 162 of the waist portion 110. The longitudinal length 156 of the space between the waist portion 100 and the central chassis portion 120 of the front panel 30 can be the same as the longitudinal length 166 of the space between the waist portion 110 and the central chassis portion 130 of the back panel 40. The absorbent article 10 can, therefore, have an asymmetrical arrangement between the front panel 30 and the back panel 40.

Figure 6:
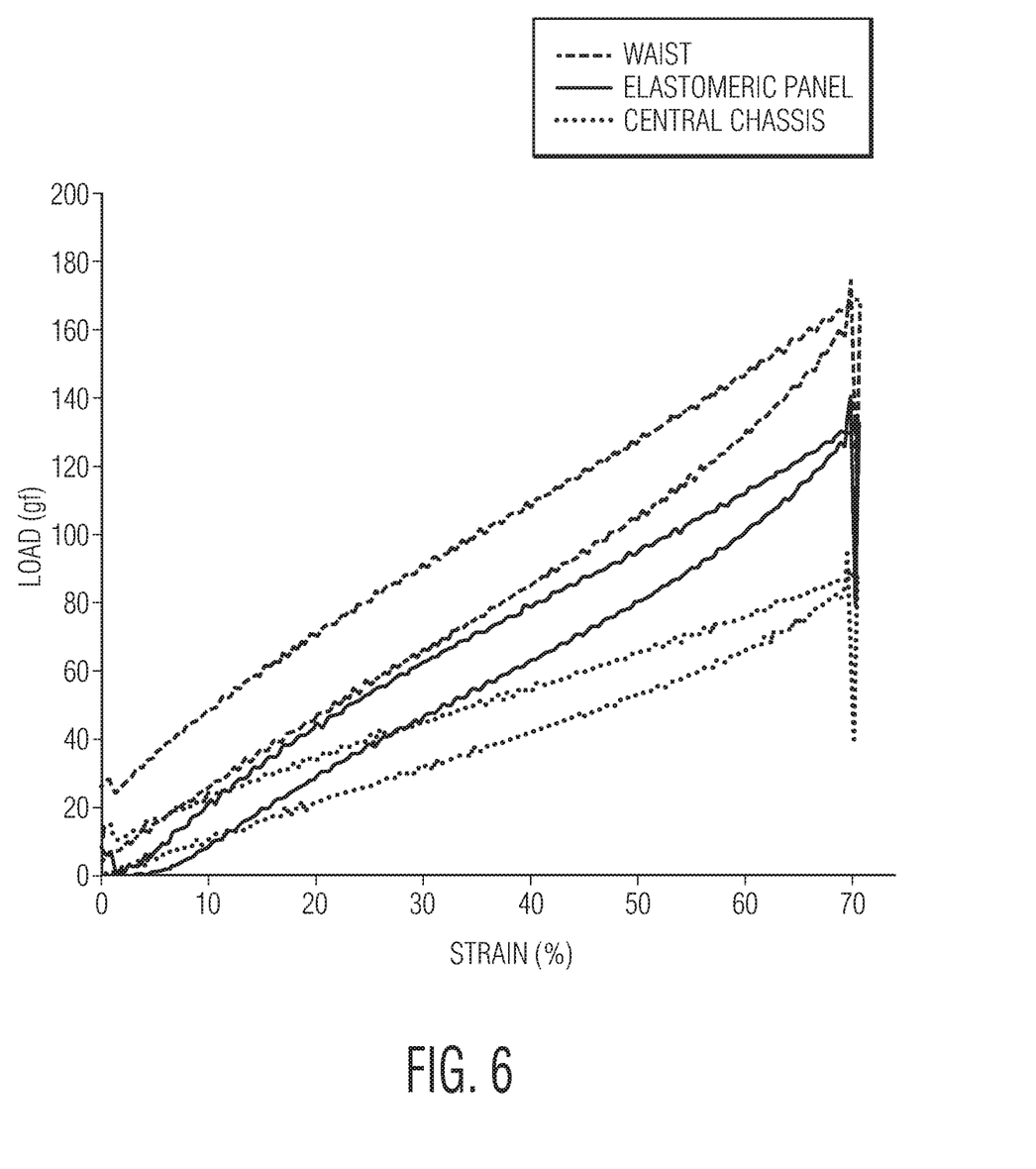
FIG. 6 is a graph depicting the load as a function of the percent strain for various portions of the absorbent article of FIG. 1.

In addition to the asymmetrical arrangement of the configuration of the front panel 30 and the back panel 40, the materials forming the front panel 30 and the back panel 40 can have different tension strains allowing for close-to-body-fit of the absorbent article 10 to the wearer of the absorbent article 10. In various embodiments, the tension strains of different regions of an absorbent article 10 can be compared by comparing the load of the regions at 50% strain according to the test method herein. The different tension strains of the materials can allow the absorbent article 10 to better conform to the curvature of the body of the wearer. Maintaining the absorbent article 10 about the waist of the wearer as well as reducing and/or eliminating leakage of body exudate from the absorbent article 10 are important attributes of an absorbent article 10. The front and back waist portions, 100 and 110, can form a complete waist region for the absorbent article 10. The front and back chassis portions, 120 and 130, can form a complete chassis region for the absorbent article 10 wherein the chassis region has variable longitudinal length. The front and back elastomeric panels, 60 and 70, can form a complete elastomeric panel region for the absorbent article 10 wherein the elastomeric panel region has variable longitudinal length. In various embodiments, the waist region can have a tension strain which can be the same as or greater than the tension strain provided by elastomeric panel region. Thus, at a 50% strain, the load of the waist region can be the same as or greater than the load at 50% strain of the elastomeric panel region. Such a tension strain provided by the waist region can maintain the absorbent article 10 in place about the waist of the wearer. At 50% strain, the load of the elastomeric panel region can be greater than the load at 50% strain of the chassis region. Such a tension strain provided by the elastomeric panel region can provide close-to-body fit of the absorbent article 10 about the legs of the wearer which can reduce the incidence of leakage of body exudate from the garment in this region of the wearer. While the absorbent article 10 needs to remain in place on the wearer and have a reduction in leakage from the leg openings, it is also an attribute of the absorbent article 10 that it be comfortable to the wearer in the regions of the buttocks, hips, and stomach. In various embodiments, at 50% strain, the load of the chassis region can be lower than the load at 50% strain of each of the waist region and the elastomeric panel region. FIG. 6 provides a graphical illustration of an example of the comparison of the waist region tension strain to the chassis region tension strain and to the elastomeric panel region tension strain. For the example illustrated in FIG. 6, at a 50% strain, the load of the waist region was greater than the load of the elastomeric panel region. Additionally, at a 50% strain, the load of the elastomeric panel region was greater than the load of the chassis region.

In various embodiments, the back panel 40 can further have multiple leg elastics 180. Each leg elastic 180 can be a single strand, ribbon, or strip of elastomeric material, such as, for example, the three strands of elastomeric material exemplified in FIGS. 4, 5A, and 5B. It is to be understood that the leg elastics 180 are optional.

As illustrated in FIGS. 1-5B, the absorbent article 10 can have an absorbent assembly 200 in the central region 24 of the absorbent article 10. At least a portion of the absorbent assembly 200 overlaps a portion of elastomeric panel 60 of the front panel 30 and at least a portion of the absorbent assembly 200 overlaps a portion of elastomeric panel 70 of the back panel 40. The absorbent assembly 200 can, therefore, be bonded to each of the overlapped regions of the elastomeric panels, 60 and 70. In various embodiments, the overlapped region of each of the elastomeric panel 60 in the front panel 30 and the elastomeric panel 70 in the back panel 40 are elastomeric. In various embodiments, at least a portion of this overlapped region of each of the elastomeric 60 of the front panel 30 and the elastomeric panel 70 of the back panel 40 is non-elastomeric.

Absorbent Assembly:

The absorbent assembly 200 can have at least a topsheet layer 202, a backsheet layer 206, and an absorbent core 208 positioned between the topsheet layer and the backsheet layer, Topsheet Layer:

The topsheet layer 202 defines a body facing surface 204 of the absorbent article 10 that may directly contact the body of the wearer and is liquid permeable to receive body exudates. The topsheet layer 202 is desirably provided for comfort and functions to direct body exudates away from the body of the wearer, through its own structure, and towards the absorbent core 208. The topsheet layer 202 desirably retains little to no liquid in its structure, so that it provides a relatively comfortable and non-irritating surface next to the skin of the wearer of the absorbent article 10.

The topsheet layer 202 can be a single layer of material, or alternatively, can be multiple layers that have been laminated together. The topsheet layer 202 can be constructed of any material such as one or more woven sheets, one or more fibrous nonwoven sheets, one or more aperture film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 202.

In various embodiments the topsheet layer 202 can be constructed from various nonwoven webs such as meltblown webs, spunbond webs, hydroentangled spunlace webs, or through air bonded carded webs. Examples of suitable topsheet layer 202 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 202 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 40, each of which is hereby incorporated by reference thereto in its entirety. Additional topsheet layer 40 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 202 may contain a plurality of apertures formed therethrough to permit body exudates to pass more readily into the absorbent core 208. The apertures may be randomly or uniformly arranged throughout the topsheet layer 202. The size, shape, diameter, and number of apertures may be varied to suit an absorbent article's 10 particular needs.

In various embodiments, the tospheet layer 202 can have a basis weight ranging from about 5, 10, 15, 20, or 25 gsm to about 50, 100, 120, 125, or 150 gsm. For example, in an embodiment, a topsheet layer 202 can be constructed from a through air bonded carded web having a basis weight ranging from about 15 gsm to about 100 gsm. In another example, a topsheet layer 202 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 202 can be at least partially hydrophilic. In various embodiments, a portion of the topsheet layer 202 can be hydrophilic and a portion of the topsheet layer 202 can be hydrophobic. In various embodiments, the portions of the topsheet layer 202 which can be hydrophobic can be either an inherently hydrophobic material or can be a material treated with a hydrophobic coating.

In various embodiments, the topsheet layer 202 can be a multicomponent topsheet layer 202 such as by having two or more different nonwoven or film materials, with the different materials placed in separate locations in the transverse direction (Y) of the absorbent article 10. For example, the topsheet layer 202 can be a two layer or multicomponent material having a central portion positioned along and straddling a longitudinal centerline of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 202 are generally described in U.S. Pat. No. 5,961, 505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 202 can be positioned symmetrically about the absorbent article 10 longitudinal centerline. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 202. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 202. The selection of such topsheet layer 202 materials can vary based upon the overall desired attributes of the topsheet layer 202. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 202 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the topsheet layer 202. The film layer may also serve as a barrier layer to prevent rewet of the topsheet layer 202 as well as to prevent the flow of fluid off the side edges of the absorbent article 10. In various embodiments, the side portions can be laminates such as a spunbond-meltblown-meltblown-spunbond layer ("SMMS") laminate, spunbond-film laminate, or alternatively, other nonwoven laminate combinations.

Absorbent Core:

An absorbent core 208 can be positioned between the topsheet layer 202 and the backsheet layer 206 of the absorbent article 10. The absorbent core 208 can generally be any single layer structure or combination of layer components, which can demonstrate some level of compressibility, conformability, be non-irritating to the wearer's skin, and capable of absorbing and retaining liquids and other body exudates. In various embodiments, the absorbent core 208 can be formed from a variety of different materials and can contain any number of desired layers. For example, the absorbent core 208 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of wood pulp fluff can be identified with the trade designation NB416, available from Weyerhaeuser Corp., and is a bleached, highly absorbent wood pulp containing primarily soft wood fibers.

In various embodiments, if desired, the absorbent core 208 can include an optional amount of superabsorbent material. Examples of suitable superabsorbent material can include poly(acrylic acid), poly(methacrylic acid), poly (acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 208 in any amount as desired.

Regardless of the combination of absorbent materials used in the absorbent core 208, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 208 can vary as desired and can comprise any one of various shapes including, but not limited to, triangular, rectangular, dog-bone, elliptical, trapezoidal, T-shape, I-shape, and hourglass shapes. In various embodiments, the absorbent core 208 can have a shape that generally corresponds with the overall shape of the absorbent article 10. The dimensions of the absorbent core 208 can be substantially similar to those of the absorbent article 10, however, it will be appreciated that the dimensions of the absorbent core 208 while similar, will often be less than those of the overall absorbent article 10, in order to be adequately contained therein.

By way of example, suitable materials and/or structures for the absorbent core 208 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al. each of which is hereby incorporated by reference thereto in its entirety.

In various embodiments, an absorbent core 208 can be a single layer structure and can include, for example, a matrix of cellulosic fluff and superabsorbent material. In various embodiments, an absorbent core 208 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 208 may be constructed of an airlaid material and the garment facing layer of the absorbent core 208 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Backsheet Layer:

The backsheet layer 206 is generally liquid impermeable and is the portion of the absorbent article 10 which faces the garments of the wearer. The backsheet layer 206 can permit the passage of air or vapor out of the absorbent article 10 while still blocking the passage of liquids. Any liquid impermeable material may generally be utilized to form the backsheet layer 206. The liquid impermeable layer 206 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the backsheet layer 206 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a backsheet layer 206 can be a polyethylene film such as that obtainable from Pliant Corp., Schaumburg, Ill., USA. Another example can include calcium carbonate-filled polypropylene film. In still another embodiment, the backsheet layer 206 can be a hydrophobic nonwoven material with water barrier properties such as a nonwoven laminate, an example of which can be a spunbond, meltblown, meltblown, spunbons, four-layered laminate.

In various embodiments, the backsheet layer 206 can be a two layer construction, including an outer layer material 210 and an inner layer material 212 which can be bonded together. The outer layer 210 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 210 can be a 20 gsm spunbond polypropylene nonwoven web. The inner layer 212 can be either vapor permeable (i.e., "breathable") or vapor impermeable. The inner layer 212 may be manufactured from a thin plastic film, although other liquid impermeable materials may also be used. The inner layer can inhibit liquid body exudates from leaking out of the absorbent article 10 and wetting articles, such as bed sheets and clothing, as well as the wearer and caregiver. An example of a material for an inner layer 212 can be a printed 19 gsm Berry Plastics XP-8695H film or equivalent commercially available from Berry Plastics Corporation, Evansville, Ind., U.S.A.

The backsheet layer 206 can, therefore, be of a single or multiple layer construction, such as of multiple film layers or laminates of film and nonwoven fibrous layers. Suitable backsheet layers 206 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Test Method:
Strain:

The materials of a fully assembled, size medium, unisex garment were tested to determine elongation or strain by utilizing a hysteresis curve for each of the waist region, chassis region, and elastomeric panel region. The fully assembled garment had a total product longitudinal length from front waist edge to back waist edge of 650 mm. The front panel of the front waist region had a longitudinal length of 185.4 mm of which the elastomeric panel had a longitudinal length of 135.4 mm, the chassis portion had a longitudinal length of 32 mm, the waist portion had a longitudinal length of 16 mm, and the space between the waist portion and the front chassis portion had a longitudinal length of 14 mm. The front chassis portion overlapped the elastomeric portion for a longitudinal length of 12 mm. The waist portion had 6 elastomeric strands sandwiched between nonwoven layers which were parallel to each other and separated by a distance of 3 mm. The front chassis portion had 4 elastomeric strands sandwich between nonwoven layers which were parallel to each other and separated by 8.3 mm. The elastomeric panel was manufactured according to U.S. Pat. No. 7,803,244. The back panel of the back waist region had a longitudinal length of 293.5 mm of which the elastomeric panel had a longitudinal length of 173.5 mm, the chassis portion had a longitudinal length of 132 mm, the waist portion had a longitudinal length of 16 mm, and the space between the waist portion and the front chassis portion had a longitudinal length of 14 mm. The front chassis portion overlapped the elastomeric portion for a longitudinal length of 12 mm. The waist portion had 6 elastomeric strands sandwiched between nonwoven layers which were parallel to each other and separated by a distance of 3 mm. The front chassis portion had 9 elastomeric strands sandwich between nonwoven layers which were parallel to each other and separated by 8.3 mm. The elastomeric panel was manufactured according to U.S. Pat. No. 7,803,244.

For this test, the sample was prepared from one fully assembled garment. The garment was positioned on two spaced apart flat bars with one of the flat bars being positioned to contact the front region and the other flat bar being positioned to contact the back region. The flat bars were moved in a direction away from each other so as to stretch the garment to a distance 20% greater than the relaxed position of the garment. While in the stretched positioned, the side seams were centrally positioned between the flat bars. Test strips will have a total length of six inches and a total width of 20 mm. To provide for the six inches in length, a total distance of six inches was measured out on the garment by measuring the garment three inches, in the transverse direction of the garment, on each side of the side seam and marking a straight line in the longitudinal direction from the waist edge to the lower edge at these measurements. To provide for the 20 mm in width, a total distance of 20 mm for each region of the garment to be tested was measured in the longitudinal transverse direction to connect the longitudinal direction markings just made above. The combination of the longitudinal direction markings and the transverse direction markings provide for rectangular shaped test strips measuring six inches by 20 mm. To provide for a test strip for the waist region, the six inches by 20 mm was marked only in the portion of the garment where waist region material was located, thus the waist region test strip being tested does not contain chassis region material. To provide for a test strip for the chassis region, the six inches by 20 mm was marked only in the portion of the garment where chassis region material was located, thus the chassis region material being tested does not include any waist region or elastomeric panel region material. To provide for a test strip for the elastomeric panel region, the six inches by 20 mm was marked only in the portion of the garment where elastomeric panel region material was located, thus the elastomeric panel region material being tested does not include any chassis region material. The elastomeric panel region test strip does not include any absorbent assembly material nor the elastomeric panel material to which the absorbent assembly was bonded. To create the test strips for each of the regions of the garment, the test strips are cut from the garment using the drawn markings as guides for the cutting lines. When marking and cutting out the waist region test strip and the chassis region test strip the most number of elastomeric strands of material are included within the rectangular shaped test strips.

The testing was done on an Advantage Pneumatic Grip Controller with a MTS Insight 1 EL 820.001-EL using TESTWORKS 4.0 software. The tests were done under ambient conditions. The grip size was 3 inches in width and 1 inch in length. Intermeshing grips were utilized so that the material would not slip while being tested. The grip separation was set at 4 inches. The test strips were loaded such that the six inch length of the sample was loaded in the vertical direction with 1 inch at each end of the sample held by the grips. A preload of approximately 10 to 15 grams was set, but zero-set before running the test. The test pulled the sample until 70% of stretch of the gage length and turned back to the zero point as one cycle. The test speed was 20 inches per minute of extension or strain. The test reported the strain for extension and retraction in percent from 0% to 70% stretch and back to 0%.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a. a front region comprising a front panel comprising:
      i. a front panel upper edge, a front panel lower edge, a first front side edge, and a second front side edge;
      ii. a first longitudinal length between the front panel upper edge and the front panel lower edge;
      iii. a first elastomeric panel comprising a first material selected from an elastomeric film, an elastomeric nonwoven web or a laminate of at least one elastomeric polymeric film layer and at least one nonwoven web layer;
      iv. a first laminate comprising elastomeric strands and a nonwoven layer and defining a front waist portion having a front waist portion longitudinal length and a front central chassis portion having a front central chassis portion longitudinal length;
   b. a back region comprising a back panel comprising:
      i. a back panel upper edge, a back panel lower edge, a first back side edge, and a second back side edge;
      ii. a second longitudinal length between the back panel upper edge and the back panel lower edge;
      iii. a second elastomeric panel comprising a second material selected from an elastomeric film, an elastomeric nonwoven web or a laminate of at least one elastomeric polymeric film layer and at least one nonwoven web layer;
      iv. a second laminate comprising elastomeric strands and a nonwoven layer and defining a back waist portion having a back waist portion longitudinal length and a back central chassis portion having a back central chassis portion longitudinal length, wherein the back central chassis portion longitudinal length is greater than the front central chassis portion longitudinal length; and
   c. a central region extending between and comprising an absorbent assembly; and
   d. wherein the first elastomeric panel has a longitudinal length that is greater than a longitudinal length of the second elastomeric panel.

2. The absorbent article of claim 1 wherein the front waist portion longitudinal length is the same as the back waist portion longitudinal length.

3. The absorbent article of claim 1 wherein the longitudinal length of the first elastomeric panel is from about 60% to about 66% of the first longitudinal length of the front panel.

4. The absorbent article of claim 1 wherein the longitudinal length of the second elastomeric panel is from about 53% to about 59% of the second longitudinal length of the back panel.

5. The absorbent article of claim 1 wherein the front central chassis portion longitudinal length is from about 15% to about 25% of the first longitudinal length of the front panel.

6. The absorbent article of claim 1 wherein the back central chassis portion longitudinal length is from about 26% to about 36% of the second longitudinal length of the back panel.

7. The absorbent article of claim 1 wherein the front waist portion comprises multiple elastomeric strands which are parallel to each other and uniformly spaced from each other.

8. The absorbent article of claim 7 wherein the spacing between each of the elastomeric strands of the front waist portion is less than 5 mm.

9. The absorbent article of claim 1 wherein the front central chassis portion comprises multiple elastomeric strands which are parallel to teach other and uniformly spaced from each other.

10. The absorbent article of claim 9 wherein the spacing between each of the elastomeric strands of the front central chassis portion is at least 5 mm.

11. The absorbent article of claim 1 wherein the front waist portion and the back waist portion combine to form a waist region and wherein the front elastomeric panel and the back elastomeric panel combine to form an elastomeric panel region and a load at 50% strain of the waist region is greater than or equal to a load at 50% strain of the elastomeric panel region.

12. The absorbent article of claim 11 wherein the front chassis portion and the back chassis portion combine to form a chassis region and a load at 50% strain of the chassis region is less than the load at 50% strain of the waist region and the elastomeric panel region.

* * * * *